United States Patent
Asaka et al.

[11] Patent Number: 5,591,837
[45] Date of Patent: Jan. 7, 1997

[54] 5-O-DESOSAMINYLERYTHRONOLIDE A DERIVATIVE

[75] Inventors: Toshifumi Asaka; Masato Kashimura; Yoko Misawa; Shigeo Morimoto; Katsuo Hatayama, all of Tokyo, Japan

[73] Assignee: Taisho Pharmaceutical Co., Ltd., Japan

[21] Appl. No.: 318,795

[22] PCT Filed: Apr. 21, 1993

[86] PCT No.: PCT/JP93/00516

§ 371 Date: Oct. 14, 1994

§ 102(e) Date: Oct. 14, 1994

[87] PCT Pub. No.: WO93/21199

PCT Pub. Date: Oct. 28, 1993

[30] Foreign Application Priority Data

Apr. 22, 1992 [JP] Japan .................................. 4-101492

[51] Int. Cl.⁶ .................................. C07H 17/08
[52] U.S. Cl. .................................. 536/7.4; 536/7.2
[58] Field of Search .................... 536/7.2, 7.4; 574/29

[56] References Cited

U.S. PATENT DOCUMENTS 5,444,051  8/1995  Agouridas et al. .................... 514/29

FOREIGN PATENT DOCUMENTS 0559896  11/1991  European Pat. Off. .
9209614  11/1992  WIPO .

OTHER PUBLICATIONS

Antimicrobial Agents & Chemotherapy vol. 5, #4, pp. 479–488.

Journal of Medicinal Chemistry vol. 17, #9, pp. 953–956 (1974).

Journal of Organic Chemistry, vol. 53 No. 10, pp. 2340–2345 (1988).

*Primary Examiner*—Elli Peselev
*Attorney, Agent, or Firm*—Lorusso & Loud

[57] ABSTRACT

Object: To provide a novel macrolide antibiotic having a strong antibacterial activity.

Constitution: 11-Amino-3,11-dideoxy-3-oxo-5-O-desosaminyl-6-O-methylerythronolide A 11-N,12-O-cyclic carbamate which has a ketone at the 3-position and a methylated hydroxyl group at the 6-position of a 5-O-desosaminylerythronolide A derivative, and pharmaceutically acceptable acid addition salts thereof.

1 Claim, No Drawings

5-O-DESOSAMINYLERYTHRONOLIDE A DERIVATIVE

DESCRIPTION

1. Technical Field

The present invention relates to a novel derivative of an antibiotic erythromycin, and more particularly relates to a novel 5-O-desosaminylerythronolide A derivative and pharmaceutically acceptable acid addition salts thereof.

2. Background of Art

Erythromycins are antibiotics clinically widely used as agents for treating infectious diseases caused by Gram-positive bacteria, some Gram-negative bacteria, mycoplasmas, etc. Many erythromycin derivatives have been prepared for the improvement of biological and pharmaceutical properties of erythromycins. Certain ketone forms at the 3-position of 5-O-desosaminylerythronolide A have been described in Antimicrobial Agents and Chemotherapy, vol. 6, No. 4, page 479 (1974) and Journal of Medicinal Chemistry, vol. 17, No. 9, page 953 (1974), but generally they have extremely weak antibacterial activity. An object of the present invention is to provide a novel antibiotic having a strong antibacterial activity.

3. Disclosure of the Invention

As a result of various researches on the antibacterial activity of 3-ketone forms of 5-O-desosaminylerythronolide A derivatives, the present inventors have found that a 5-O-desosaminylerythronolide A derivative, which falls within the formula of the specification of EP patent No. 0487411 but is not specifically described therein, has a extremely strong antibacterial activity, and the present invention has been accomplished.

The present invention relates to 11-amino-3,11-dideoxy-3-oxo-5-O-desosaminyl-6-O-methyl-erythronolide A 11-N,12-O-cyclic carbamate and a pharmaceutically acceptable acid addition salt thereof.

In the present invention, the pharmaceutically acceptable acid addition salt means, for example, acetate, propionate, butyrate, formate, trifluoroacetate, maleate, tartrate, citrate, stearate, succinate, ethylsuccinate, lactobionate, gluconate, glucoheptonate, benzoate, methanesulfonate, ethanesulfonate, 2-hydroxyethanesulfonate, benzenesulfonate, p-toluenesulfonate, laurylsulfate, malate, aspartate, glutaminate, adipate, cysteine salt, hydrochloride, hydrobromide, phosphate, sulfate, hydroiodide, nicotinate, oxalate, picrate, thiocyanate, undecanoate, polyacrylate or carboxyvinyl polymer salt.

The compounds of the present invention can be prepared, for example, as follows.

Preparation Method 1

Method using 6-O-methyl-erythromycin A as a starting material

Step (1); 6-O-Methylerythromycin A is first reacted with an acid anhydride represented by the formula $R_2O$ (wherein R is an acetyl group or a propionyl group) or an acid halide represented by the formula RX (wherein R is as defined above, and X is a halogen atom) and a base in an inert solvent at from 0° C. to 30° C. for protection of the hydroxyl groups at the 2'- and 4"-positions at the same time to give a compound represented by the formula (a):

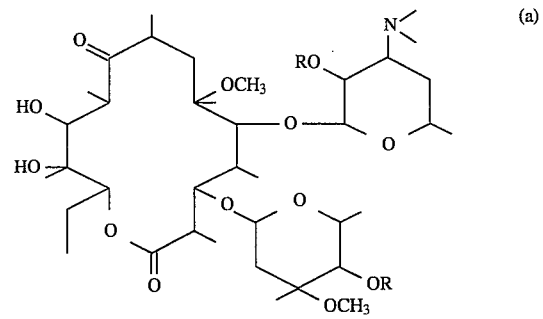

(wherein R is as defined above). Preferable examples of the inert solvent to be used herein are dichloromethane, dichloroethane, acetone and pyridine. The acid anhydride and acid halide to be used are those of acetic acid and propionic acid. Examples of the base to be used are pyridine and 4-dimethylaminopyridine.

Step (2); The compound (a) is reacted with 1,1'-carbonyldiimidazole and a base in a suitable solvent at room temperature to give a compound represented by the formula (b):

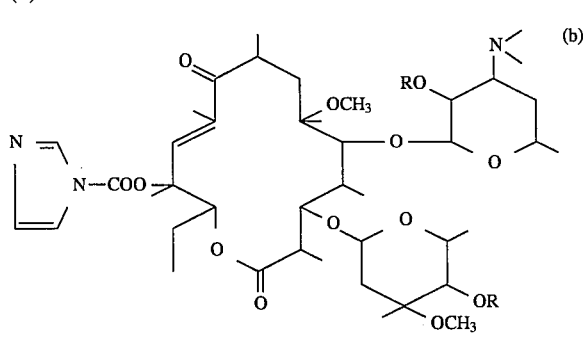

(wherein R is as defined above). Examples of the suitable solvent to be used herein are N,N-dimethylformamide, N-methylpyrrolidone, tetrahydrofuran, acetonitrile and a mixture thereof. Examples of the base to be used are sodium hydride, potassium hydroxide and sodium bis-trimethylsilylamide.

Step (3); The compound (b) is reacted by adding ammonia and sodium hydride in a suitable solvent to give an 11,12-cyclic carbamate represented by the formula (c):

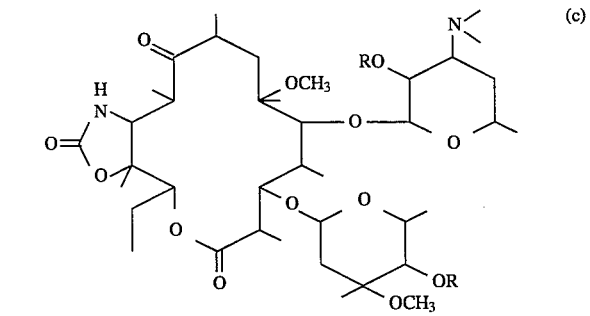

(wherein R is as defined above). The inert solvent to be used herein is the same as used in Step (2).

Step (4); The compound (c) is reacted with an acid to give a compound of the formula (d):

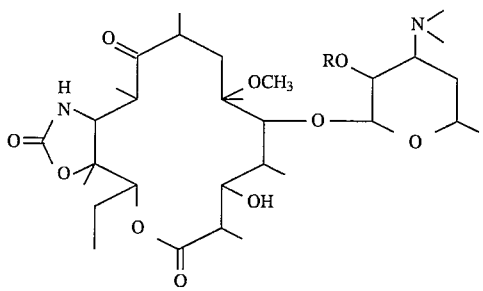

(wherein R is as defined above). Examples of the acid to be used herein include hydrochloric acid, hydrobromic acid and sulfuric acid, preferably 0.5–2N hydrochloric acid, if desired, a mixture of one of these acids with a lower alcohol such as, for example, methanol or ethanol.

Step (5); The compound (d) is oxidized in an inert solvent by using chromic acid, chromic acid-pyridine, pyridinium chlorochromate, pyridinium dichromate, activated dimethylsulfoxide and the like at −78° C. to 30° C. to give a 3-ketone form. Then, the compound is reacted in a lower alcohol or a mixture of a lower alcohol with water, if desired, by adding a base such as sodium bicarbonate, at 0° C. to 100° C., preferably room temperature to 80° C. for removal of the protective group at the 2'-position to give a compound of the present invention represented by the formula (e):

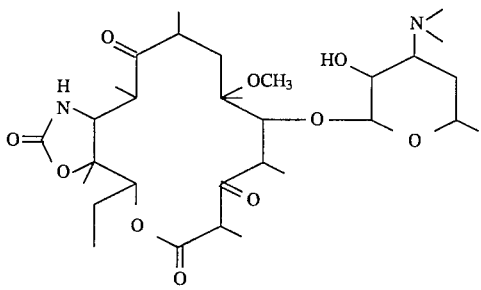

The inert solvent to be used herein is the same as used in Step (1). Examples of an activating agent of dimethylsulfoxide are acetic anhydride, trifluoroacetic anhydride, oxalyl chloride, phosphorus pentachloride, pyridinium sulfate, pyridinium trifluoroacetate, 1,3-dicyclohexylcarbodiimide and 1-(3-dimethylamino-propyl)-3-ethylcarbodiimide hydrochloride. Examples of the lower alcohol to be used herein are methanol, ethanol and propyl alcohol.

Preparation Method 2

Method using 5-O-desosaminyl-6-O-methylerythronolide A as a starting material

Step (6); 5-O-Desosaminyl-6-O-methylerythronolide A is first reacted with an acid anhydride represented by the formula $R_2O$ (wherein R is as defined above) in an inert solvent, if desired, in the presence of a weak base such as sodium bicarbonate for protection of only the hydroxyl group at the 2'-position, and then reacted by using a reagent such as phosgene dimer or phosgene trimer and a base in an inert solvent under ice cooling. To the reaction mixture is added excess benzyl alcohol, the temperature of which is allowed to turn to room temperature, and stirring results in the 11,12-cyclic carbonation and benzyloxycarbonylation at the 3-position in the same vessel to give a compound of the formula (f):

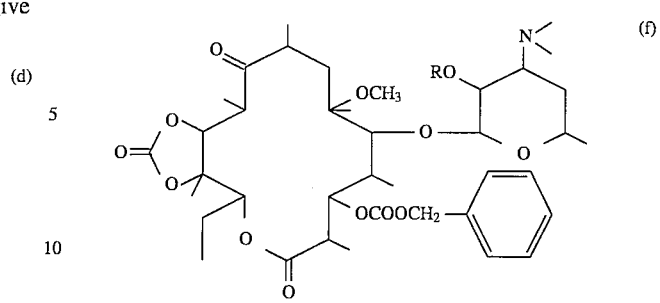

(wherein R is as defined above). The inert solvent to be used herein is the same as used in Step (1). Examples of the base to be used are pyridine, colidine, N-methylpiperidine, N-methylmorpholine, triethylamine and dimethylaniline. This compound is then reacted in the same manner as that of Step (2) to give a compound represented by the formula (g):

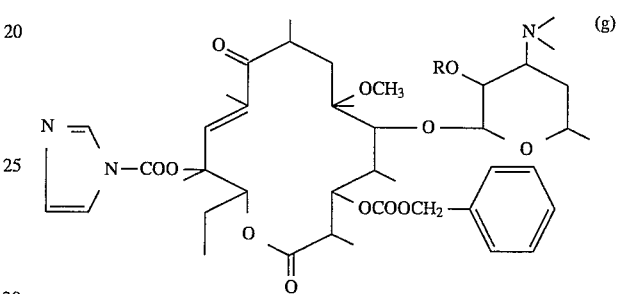

(wherein R is as defined above).

Step (7); The compound (g) is reacted in the same manner as that of Step (3) to give an 11,12-cyclic carbamate. To this compound is added 10% Pd-C and ammonium formate, and the mixture is stirred for removal of the benzyloxycarbonyl group at the 3-position, followed by reacting in the same manner as that of Step (5) to give a compound of the present invention.

The compounds of the present invention can be administered orally or parenterally in the dosage form such as, for example, tablets, capsules, powders, troches, ointments, suspensions, supositories or injections, all of which can be prepared by conventional preparation techniques. The daily dose is from 1 mg/kg to 50 mg/kg, which is administered in a single dose or 2–3 divided doses.

INDUSTRIAL UTILIZATION

The compounds of the present invention have a strong antibacterial activity against erythromycin-sensitive bacteria and certain resistant bacteria, and have good absorbability in the body. Therefore, the compounds of the present invention are useful as antibacterial agents for the treatment of infectious diseases caused by bacteria in human beings and animals (including farm animals).

BEST MODE FOR CARRYING OUT THE INVENTION

The present invention is illustrated in more detail by the following examples.

EXAMPLE 1

(1) To a solution of 500 g (0.668 mole) of 6-O-methylerythromycin A in 1 L of dichloromethane were added 220.8 ml (2.34 moles) of acetic anhydride and 32.67 g (0.267 mole) of 4-dimethylaminopyridine, followed by stirring at room temperature for 2 hours. The reaction solution was washed with dil. sodium hydroxide solution, and dried over anhydrous sulfated magnesium. The solvent was evaporated, and the resulting crude crystals were crystallized from ethyl acetate to give 485.2 g of 2',4"-di-O-acetyl-6-O-methylerythromycin A.

(2) To a solution of 149.77 g (0.18 mole) of the compound obtained in the above (1) in a mixture of 225 ml of N,N-dimethylformamide and 375 ml of tetrahydrofuran was added 73.08 g (0.45 mole) of 1,1'-carbonyldiimidazole. 9.37 g (0.23 mole) of 60% sodium hydride was added under ice cooling at 5°–7° C., followed stirring for an hour. The temperature was allowed to turn to room temperature, the mixture was allowed to react for 2.5 hours. Extraction with ethyl acetate gave 200.79 g of 10,11-anhydro-2',4"-di-O-acetyl-12-O-imidazolylcarbonyl-6-O-methylerythromycin A as a colorless foam.

(3) A solution of 200.79 g of the compound obtained in the above (2) in 400 ml of tetrahydrofuran was added dropwise to a mixture of 500 ml of liquid ammonia and 200 ml of tetrahydrofuran under dry-ice acetone cooling, followed by stirring at room temperature for 2 days. 2.16 g (0.054 mole) of 60% sodium hydride was added, and the mixture was allowed to react for 3 hours. Extraction with ethyl acetate gave 174.35 g of 11-amino-11-deoxy-2',4"-di-O-acetyl-6-O-methylerythromycin A 11-N,12-O-cyclic carbamate as a colorless crystalline powder.

(4) 174.35 g (0.20 mole) of the compound obtained in the above (3) was dissolved in a mixture of 700 ml of 2N hydrochloric acid and 350 ml of ethanol, followed by stirring at room temperature for 20 hours. 350 ml of 4N sodium hydroxide solution was added, and the precipitated crude crystals were collected by filtration and purified by silica gel column chromatography (eluent; hexane:acetone:triethylamine=100:50:0.2) to give 116.2 g of 2'-O-acetyl-11-amino-11-deoxy-5-O-desosaminyl-6-O-methylerythronolide A 11-N,12-O-cyclic carbamate.

(5) To a solution of 110.84 g (0.16 mole) of the compound obtained in the above (4) in 600 ml of dichloromethane were added 76.68 g (0.40 mole) of 1-(3-dimethylaminopropyl)-3-ethylcarbodiimide hydrochloride and 90.8 ml (1.28 moles) of dimethyl sulfoxide under ice cooling. Then, 77.25 g (0.40 mole) of pyridinium trifluoroacetate was added, followed by stirring for 1.5 hours. After completion of the reaction, the dichloromethane layer was washed with a saturated aqueous sodium chloride solution and a saturated sodium bicarbonate solution successively, and the dichloromethane was evaporated under reduced pressure. The residue was dissolved in 300 ml of methanol, and heated under reflux for 3 hours. The methanol was evaporated, and the resulting crude product was purified by silica gel column chromatography (eluent; a chloroform solution containing 1.5–8% methanol) and crystallized from methanol to give 62.28 g of 11-amino-3,11-dideoxy-3-oxo-5-O-desosaminyl-6-O-methylerythronolide A 11-N,12-O-cyclic carbamate as colorless crystals.

mp: 245~247° C.

Mass (FAB) m/z: 613 [MH]$^+$ $^1$H-NMR (300 MHz, CDCl$_3$) δ (ppm):

1.32 (3H, s), 1.48 (3H, s), 2.29 (6H, s), 2.61 (3H, s)

$^{13}$C-NMR (75 MHz, CDCl$_3$) δ (ppm):

40.3 [3'-N(CH$_3$)$_2$], 49.4 (6-OCH$_3$), 158.0 (11-NCOO-12), 204.5 (C-3)

EXAMPLE 2

(1) To a solution of 11.78 g (0.02 mole) of 5-O-desosaminyl-6-O-methylerythronolide A in 100 ml of acetone was added 2.27 ml (0.024 mole) of acetic anhydride under ice cooling, followed by stirring at room temperature for 6 hours. The acetone was evaporated under reduced pressure, and the residue was extracted with dichloromethane. The dichloromethane layer was washed with a saturated sodium bicarbonate solution and a saturated aqueous sodium chloride solution successively, and dried over anhydrous magnesium sulfate. The solvent was evaporated under reduced pressure, and the residue was recrystallized from ether—n-hexane to give 12.17 g of 2'-O-acetyl-5-O-desosaminyl-6-O-methylerythronolide A as a white powder.

mp: 158°~160° C.

Mass (FAB) m/z: 632 [MH]$^+$ $^1$H-NMR (200 MHz, CDCl$_3$) δ (ppm):

2.07 (3H, s), 2.26 (6H, s), 2.95 (3H, s), 3.26 (1H, s), 3.96 (1H, s)

IR (KBr, cm$^{-1}$): 3469, 1750, 1733, 1693

(2) To a solution of 42.5 g (67.3 mmoles) of the compound as obtained in the above (1) in 230 ml of dichloromethane was added 81.4 ml (1.01 moles) of pyridine under ice cooling. A solution of 20.2 ml (168 mmoles) of trichloromethyl chloroformate in 20 ml of dichloromethane was added dropwise at the same temperature, and after stirring for 3 hours, 72.7 ml (673 mmoles) of benzyl alcohol was added dropwise over 30 minutes. After stirring at room temperature for 16 hours, ice pieces were added gradually. The mixture was adjusted to pH 10 with a sodium hydroxide solution. The dichloromethane was evaporated under reduced pressure, and the residue was extracted with ethyl acetate. The ethyl acetate layer was washed with a saturated aqueous sodium chloride solution, and dried over anhydrous magnesium sulfate. The solvent was concentrated to 300 ml under reduced pressure, and the precipitated crystals were collected by filtration to give 38.7 g of 2'-O-acetyl-3-O-benzyloxycarbonyl-5-O-desosaminyl-6-O-methylerythronolide A 11,12-cyclic carbonate.

Mass (FAB) m/z: 792 [MH]$^+$ $^1$H-NMR (300 MHz, CDCl$_3$) δ (ppm):

1.49 (3H, s), 2.07 (3H, s), 2.25 (6H, s), 2.99 (3H, s), 4.70 (1H, s), 5.21 (2H, s), 7.35~7.46 (5H, m)

IR (KBr, cm$^{-1}$): 1821, 1746, 1715, 1267, 1241

(3) To a solution of 10 g (12.6 mmoles) of the compound obtained in the above (2) in 100 ml of N,N-dimethylforamide—tetrahydrofuran (1:1) were added 8.18 g (50.4 mmoles) of 1,1'-carbonyldiimidazole and 1.11 g (27.8 mmoles) of 60% sodium hydride, followed by stirring at room temperature for 0.5 hour. The tetrahydrofuran was evaporated under reduced pressure, and water was added to the residue, followed by extraction with ethyl acetate. The organic layer was washed with water and a saturated aqueous sodium chloride solution successively, and dried over anhydrous magnesium sulfate. Evaporation of the solvent gave 11.5 g of 2'-O-acetyl-10,11-anhydro-3-O-benzyloxycarbonyl-12-O-imidazolylcarbonyl-5-O-desosaminyl-6-O-methyl-erythronolide A as a white foam.

(4) To a solution of 5 g (5.9 mmoles) of the compound obtained in the above (3) in a mixture of 50 ml of acetonitrile and 5 ml of tetrahydrofuran was added 3 ml of 25% aqueous ammonia, followed by stirring at room temperature for 4 days. The mixture, after addition of water, was extracted with ethyl acetate. The organic layer was washed with water and a saturated aqueous sodium chloride solution successively, and dried over anhydrous magnesium sulfate. The solvent was evaporated, and the residue was purified by silica gel column chromatography (eluent; chloroform:acetone=3:1) to give 1.8 g of a cyclic carbamate, which was then heated in methanol for 2 hours to give 0.95 g of a compound which was removed the acetyl group at the 2'-position.

(5) To a solution of 0.85 g (1.14 mmoles) of the compound obtained in the above (4) in 10 ml of methanol were added 0.17 g of 10% pd-C (ratio of 20% by weight) and 358 mg (5.70 mmoles) of ammonium formate, followed by stirring at room temperature for 0.5 hour. The reaction solution was filtered, and the filtrate was concentrated. The methanol was evaporated under reduced pressure, water was poured into the residue, and the mixture was extracted with ethyl acetate. The organic layer was washed with water and a saturated aqueous sodium chloride solution successively, and dried over anhydrous magnesium sulfate solution. Evaporation of the solvent gave 0.64 g of a compound having a hydroxyl group at the 3-position.

(6) To a solution of 0.6 g (0.98 mmole) of this compound in 6 ml of acetone was added 0.15 ml (2.28 mmoles) of acetic anhydride, followed by stirring at room temperature for 1.5 hours. The acetone was evaporated under reduced pressure, and the residue was worked up in the same manner as that of the above (5) to give 0.58 g of a 2'-acetyl compound.

(7) To a solution of 0.29 g (0.44 mmole) of the compound obtained in the above (6) in 3 ml of dichloromethane were added 0.3 ml (4.23 mmoles) of dimethyl sulfoxide, 0.254 g (1.32 mmoles) of 1-ethyl-3-(3-dimethylaminopropyl)carbodiimide hydrochloride and 0.256 g (1.33 mmoles) of pyridinium trifluoroacetate, followed by stirring at room temperature for an hour. The reaction solution, after addition of 2N sodium hydroxide solution and water, was extracted with dichloromethane. The organic layer was worked up in the same manner as that of the above (5). The solvent was evaporated, 10 ml of methanol was added to the resulting residue, and the mixture was heated under reflux for 2 hours. The methanol was evaporated, and the resulting residue was purified by silica gel column chromatography (eluent; chloroform:methanol:25% aqueous ammonia=30:1:0.1), and crystallized from dichloromethane—n-hexane to give 0.16 g of 11-amino-3,11-dideoxy-3-oxo-5-O-desosaminyl-6-O-methylerythronolide A 11-N,12-O-cyclic carbamate.

EXPERIMENT 1

In Vitro Antibacterial Activity

The in vitro antibacterial activity of the compound of the present invention against various experimental microorganism was measured using sensitive disc media (produced by Eiken Chemical Co.) according to the MIC measuring method specified by the Japan Chemotherpeutic Society. Comparative drug 1:3-deoxy-11-{2-[methyl(benzyl)amino]ethyl}amino-3-oxo-5-O-desosaminyl-6-O-methylerythronolide A 11-N,12-O-cyclic carbamate (described in EP patent No. 0487411), Comparative drug 2:3-deoxy-3-oxo-5-O-desosaminyl-6-O-methylerythronolide A 11,12-cyclic carbonate (described in EP patent No. 0487411), Comparative drug 3:6-O-methylerythromycin A and Comparative drug 4:azithromycin were used. The results are expressed as MIC value (Minimum Inhibitory Concentration, mcg/ml), and shown in Table 1.

TABLE 1

| | In vitro antibacterial activity MIC value (mcg/ml) | | | | |
|---|---|---|---|---|---|
| | Compound | | | | |
| Microorganism | Compound 1 | Comparative drug 1 | Comparative drug 2 | Comparative drug 3 | Comparative drug 4 |
| S. aureus 209P-JC | 0.05 | 0.10 | 0.10 | 0.10 | 20.0 |
| S. aureus Smith 4 | 0.10 | 0.10 | 0.10 | 0.10 | 0.39 |
| E. faecalis CSJ 1212 | 0.05 | 0.10 | 0.05 | 3.13 | 6.25 |
| S. aureus B1 | 0.20 | 0.39 | 1.56 | >100 | >100 |
| H. influenzae ATCC19418 | 6.25 | 6.25 | 25 | 12.5 | 6.25 |

Compound 1: The compound of the present invention (11-Amino-3,11-dideoxy-3-oxo-5-O-desosaminyl-6-O-methylerythronolide A 11-N,12-O-cyclic carbamate)

EXPERIMENT 2

In Vivo Antibacterial Activity

The injection protection effect of the compound of the present invention against infectious bacteria (S. aureus Smith 4) was studied using 8 male ICR mice, 4-week-old, for each group and using Comparative drugs 1, 2 and 3 (as described in Experiment 1). Infectious bacteria (S. aureus Smith 4) were incubated for 18 hours, and diluted with a saline solution containing 5% mucin and heart infusion agar, and 0.5 ml of which was inoculated intraperitoneally to mice. An hour after inoculation of bacteria, the drug suspended in 5% gum arabic was administered orally, followed by judgement of life and death during 7 days. The results are shown in Table 2.

TABLE 2

| | Number of Survival (n = 8) | | |
|---|---|---|---|
| | Dose (mg/mouse) | | |
| Microorganism | 0.1 | 0.4 | 1.6 |
| Compound 1 | 8 | 8 | 8 |
| Comparative drug 1 | 2 | 2 | 7 |
| Comparative drug 2 | 2 | 8 | 8 |
| Comparative drug 3 | 3 | 6 | 8 |

EXPERIMENT 3

Concentration in Mouse Serum

Concentration of the compound of the present invention in mouse serum was determined by using 10 male ICR mice, 4-week-old, for each group and using Comparative drugs 2 and 3 (as described in Experiment 1). The drug suspended in 5% gum arabic was administered orally to mice, the blood was collected with lapse of time, and the serum was separated. Concentration of the drug in the serum was measured by using M. luteus ATCC 9341 as approved bacteria according to the papar-disc method. The results are shown in Table 3.

TABLE 3

| Time (hr) | 0.25 | 0.50 | 1 (mcg/ml) | 2 | 4 | 6 | Cmax (mcg/ml) | AUC (mcg.h/ml) |
|---|---|---|---|---|---|---|---|---|
| Compound 1 | 0.23 | 1.17 | 0.77 | 0.60 | 0.44 | 0.05 | 1.17 | 2.90 |
| Comparative drug 2 | 0.31 | 0.41 | 0.27 | 0.28 | 0.26 | 0 | 0.41 | 1.37 |
| Comparative drug 3 | 0.29 | 0.33 | 0.34 | 0.11 | 0.11 | 0.04 | 0.34 | 0.88 |

We claim:

1. 11-Amino3,11-dideoxy-3-oxo-5-O-desosaminyl-6-O-methylerythronolide A 11-N,12-O-cyclic carbamate or a pharmaceutically acceptable acid addition salt thereof.

* * * * *

UNITED STATES PATENT AND TRADEMARK OFFICE
CERTIFICATE OF CORRECTION

PATENT NO. : 5,591,837
DATED : January 7, 1997
INVENTOR(S) : ASAKA et al

It is certified that error appears in the above-indentified patent and that said Letters Patent is hereby corrected as shown below:

Col. 8, Table 1, under the heading "Comparative drug 4", "20.0" should read --0.20--.

Col. 9, line 11, "11-Amino3" should read --11-Amino-3--.

Signed and Sealed this

Eleventh Day of November, 1997

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,591,837
DATED : January 7, 1997
INVENTOR(S) : ASAKA et al

It is certified that error appears in the above-identified patent and that said Letters Patent is hereby corrected as shown below:

On the title page, item [56], under the heading "OTHER PUBLICATIONS", "Antimicrobial Agents & Chemotherapy vol. 5, #4" should read --Antimicrobial Agents & Chemotherapy vol. 6, #4--.

Signed and Sealed this

Nineteenth Day of December, 2000

Attest:

Q. TODD DICKINSON

*Attesting Officer*  *Commissioner of Patents and Trademarks*